(12) United States Patent
Cho et al.

(10) Patent No.: US 9,175,328 B2
(45) Date of Patent: Nov. 3, 2015

(54) ELECTRON TRANSFER MEDIATORS FOR ENZYME-BASED BIOSENSOR

(71) Applicants: Samsung Electronics Co., Ltd., Gyeonggi-do (KR); Institute for Research & Industry Cooperation, PNU, Busan (KR)

(72) Inventors: Chulho Cho, Gyeonggi-do (KR); Yoon-bo Shim, Busan (KR); Jaegeol Cho, Gyeonggi-do (KR)

(73) Assignees: Samsung Electronics Co., Ltd. (KR); Institute for Research & Industry Cooperation, PNU (KR)

( * ) Notice: Subject to any disclaimer, the term of this patent is extended or adjusted under 35 U.S.C. 154(b) by 215 days.

(21) Appl. No.: 14/052,148

(22) Filed: Oct. 11, 2013

(65) Prior Publication Data
US 2014/0102896 A1   Apr. 17, 2014

(30) Foreign Application Priority Data
Oct. 11, 2012   (KR) .................. 10-2012-0113132

(51) Int. Cl.
*C12Q 1/00* (2006.01)
*G01N 27/327* (2006.01)
*C07F 15/02* (2006.01)

(52) U.S. Cl.
CPC .............. *C12Q 1/004* (2013.01); *C07F 15/025* (2013.01); *G01N 27/327* (2013.01)

(58) Field of Classification Search
None
See application file for complete search history.

(56) References Cited

U.S. PATENT DOCUMENTS

2009/0095625 A1* 4/2009 Forrow .................... 204/403.14
2011/0100467 A1* 5/2011 Kakita et al. ................. 136/263

* cited by examiner

*Primary Examiner* — Jennifer Dieterle
(74) *Attorney, Agent, or Firm* — The Farrell Law Firm, P.C.

(57) ABSTRACT

A new ferrous complex capable of being used as an electron transfer mediator for a glucose sensor, a biosensor, and the like, is provided, which measure a glucose concentration in blood, in which the new ferrous complex exchanges rapidly and smoothly an electron between an enzyme and electrode, is strongly absorbed into electrode, and is stable, so that the new ferrous complex allows excellent sensitivity of a glucose sensor to be maintained.

12 Claims, 10 Drawing Sheets

ELECTRON TRANSFER MEDIATORS FOR ENZYME-BASED BIOSENSOR

PRIORITY

This application claims priority under 35 USC §119(a) to a Korean Patent Application filed in the Korean Intellectual Property Office on Oct. 11, 2012, and assigned Serial No. 2012-0113132, the entire disclosure of which is incorporated herein by reference.

BACKGROUND OF THE INVENTION

1. Field of the Invention

The present invention generally relates to new ferrous complexes capable of being used as an electron transfer mediator in an enzyme-based biosensor, and more particularly, as an electron transfer mediator, the new ferrous complexes exchange an electron rapidly and smoothly between an enzyme and electrode, are strongly absorbed onto electrode and are stable, so that the new ferrous complexes allow excellent sensitivity of a biosensor to be maintained.

2. Description of the Related Art

In general, an electrochemical biosensor is a device for detecting various analysis objects in the environment, as well as in the fields of biology, medical science, and the like, and representatively, there is a biosensor for detecting analytes such as glucose, cholesterol, amino acids, and the like from human body fluids.

A glucose sensor is a type of biosensor, which is a device for measuring the concentration of glucose in blood or urine, and is used for diagnosing diabetes, or the like. Present commercially available electrochemical glucose sensors use mainly enzyme electrodes, and more specifically, have a structure whereby glucose oxidase is fixed on an electrode capable of converting electrical signals by using a chemical or physical method. As a basic principle, such an electrochemical glucose sensor measures the concentration of glucose in analytes by measuring current generated through transfer of electrons to the electrode, wherein the electrons are generated by oxidizing glucose in an analyte such as blood with enzymes.

In the case of a biosensor using an enzyme electrode, there is a problem that since the distance from an active center of the enzyme is too long, it is difficult to directly transfer electrons generated by an oxidization of the substrate to the electrode. Accordingly, an oxidation and reduction mediator, that is, an electron transfer mediator, is necessarily needed in order to easily perform such an electron transfer reaction.

Conventionally, examples of representative electron transfer mediators that are typically used include ferrocene, ferrocene derivatives, quinone derivatives, osmium derivatives, potassium ferricyanide, and the like. Among them, ferricyanide as a representative electron transfer mediator applied in commercially available biosensors is an anion that is bonded with six cyanide ligands around $Fe^{3+}$ in an octahedral structure, and is easily oxidized with $[Fe(CN)_6]^{4-}$, in which its oxidation and reduction are reversible. Because of these properties, ferricyanide serves as a good representative electron transfer material in the electrochemical field, and is mainly used as an electron transfer mediator for biosensors. However, problems occur when ferricyanide is not strongly absorbed into the surface of electrode, and thereby is exposed to the solution, where it tends to be eliminated into the solution. Thus an amount of the electron transfer mediator available for a reaction with enzymes is reduced, thereby decreasing measurement sensitivity of blood glucose for a glucose sensor. For this reason, it is difficult to measure blood glucose accurately.

SUMMARY OF THE INVENTION

The present invention has been made to address at least the above described problems and disadvantages, and to provide at least the advantages described below. Accordingly, an aspect of the present invention provides an electron transfer mediator that is strongly absorbed onto electrode and thereby not eliminated in the solution for use with a biosensor.

Another aspect of the present invention provides a synthesized 5-(2,5-di(thiophen-2-yl)-1H-pyrrol-1-yl)-1,10-phenanthroline Iron (III) Chloride, a new ferrous complex, having strong absorbability and excellent sensitivity according to the present invention.

Another aspect of the present invention provides such a new ferrous complex, in which, as an electron transfer mediator for a biosensor, in particular a glucose sensor, the new ferrous complex exchanges electrons rapidly and smoothly between an enzyme and electrode, is strongly absorbed onto electrode, and is stable, so that the new ferrous complex allows excellent sensitivity of the glucose sensor to be maintained.

According to an aspect of the present invention a new ferrous complex is provided, 5-(2,5-di(thiophen-2-yl)-1H-pyrrol-1-yl)-1,10-phenanthroline Iron (III) Chloride, represented by the following Chemical Formula 1:

Chemical Formula 1

Regarding the ferrous complex, a functional group of $Fe^{2+/3+}$ is introduced to a functional electrically conductive monomer having a thiophene-pyrrole linear bonding as a basic backbone, and the ferrous complex may be used as an electron transfer mediator for an enzyme-based biosensor. The electron transfer mediator functions to help an electron transfer between an enzyme and an electrode for an enzyme-based biosensor. The ferrous complex may be physically or chemically fixed on the electrode for an enzyme-based glucose sensor. In addition, the ferrous complex may be used as an electron transfer mediator exhibiting strong absorbability and excellent sensitivity caused by strongly absorbing onto the electrode.

As for the enzyme-based biosensor, the electrode may be selected from the group consisting of carbon electrode, gold electrode, copper electrode, and palladium electrode. However, the present invention is not limited thereto.

As for the enzyme-based biosensor, the enzyme may be changed according to an object to be measured by a biosensor. For example, in a case in which cholesterol, alcohol, or glucose in blood is measured as an object, a cholesterol degrading enzyme, an alcohol degrading enzyme, or a glucose degrading enzyme may be used, respectively. Accordingly, for a glucose sensor according to an example of the present invention, an enzyme for oxidizing glucose may be used. Examples thereof may be selected from the group consisting of glucose oxidase, glucose dehydrogenase, glucose hexokinase, glutamic oxaloacetic transaminase, and glutamic pyruvic transaminase. However, the present invention is not limited thereto.

Figure 1:
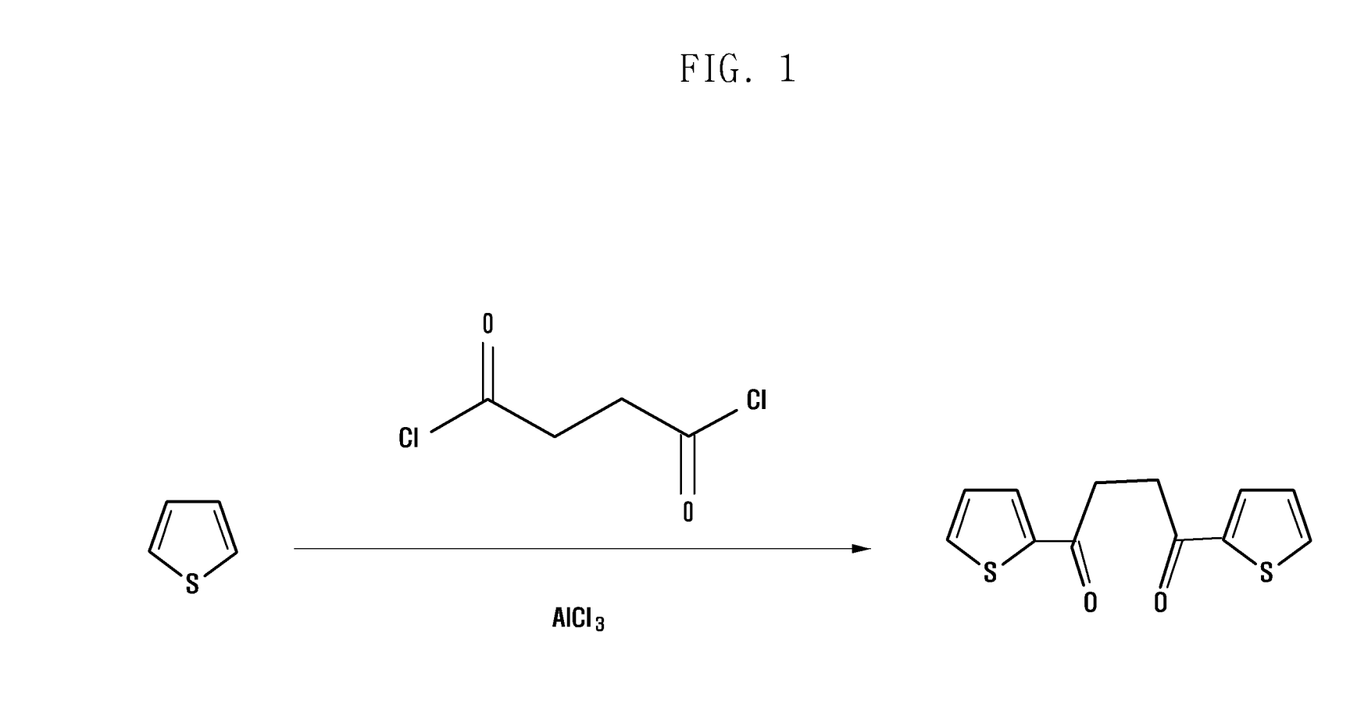
FIG. 1 is a diagram schematically illustrating a process of synthesizing 4-di(2-thienyl)-1,4-butanedione according to Example 1.
Figure 2:
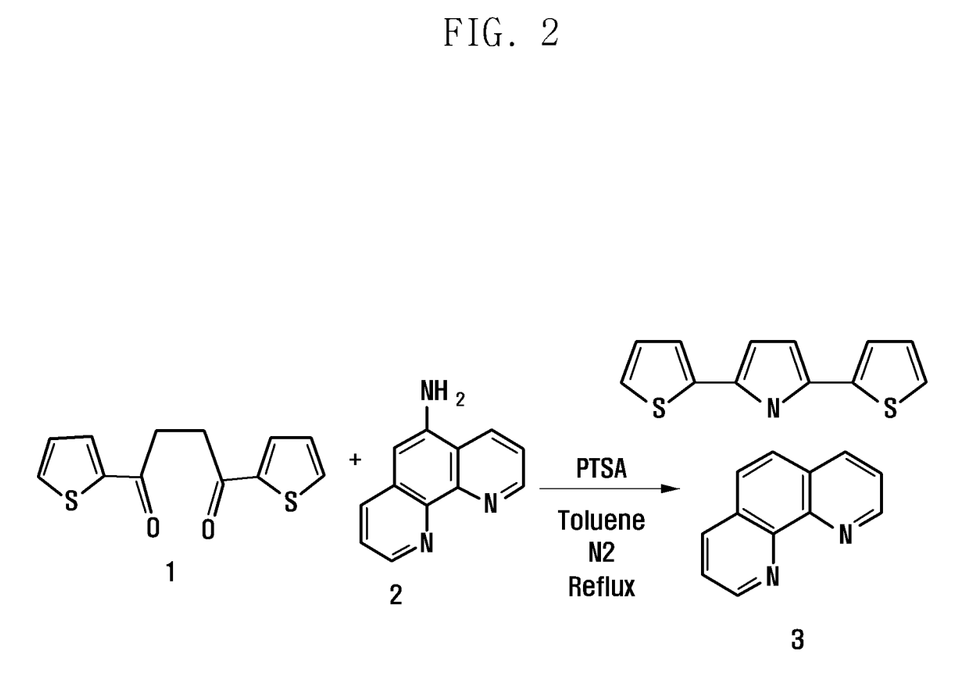
FIG. 2 is a diagram schematically illustrating a process of synthesizing 5-di(thiophen-2-yl)-1H-pyrrol-1-yl)-1,10-phenanthroline according to Example 1.
Figure 3:
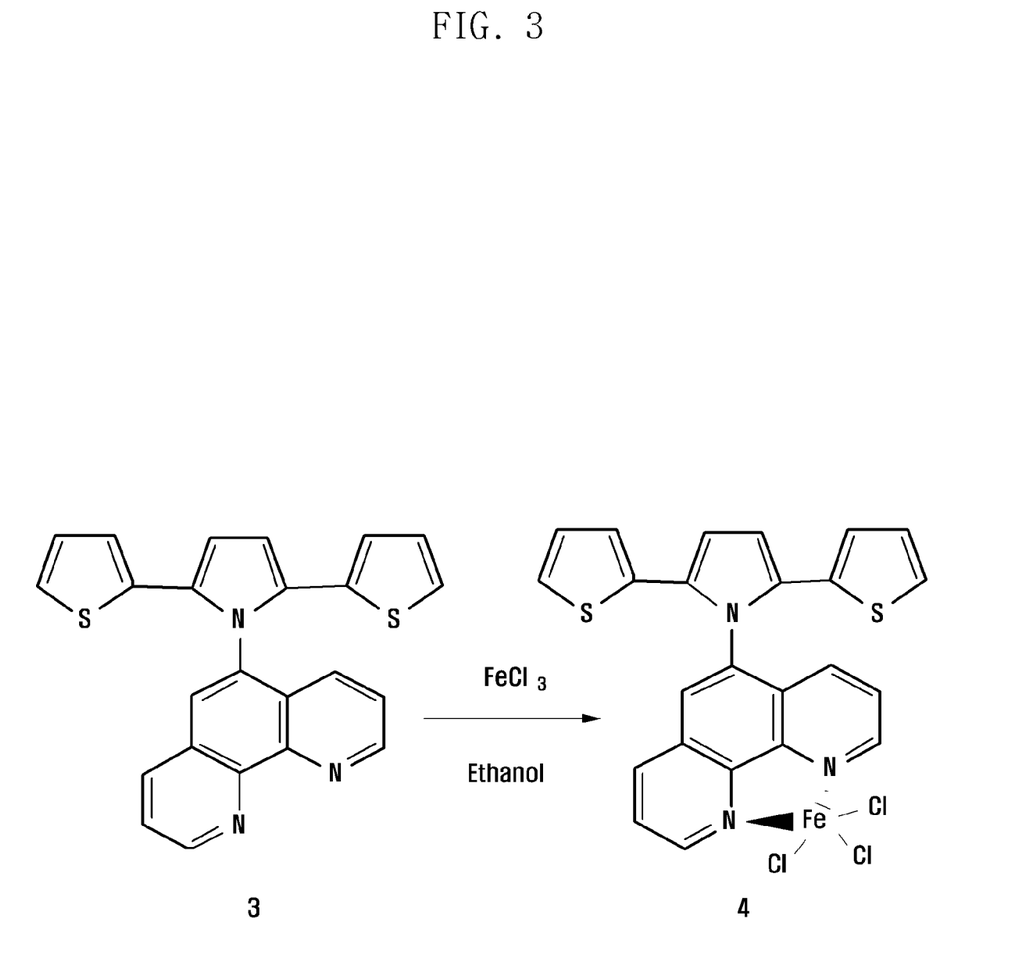
FIG. 3 is a diagram schematically illustrating a process of synthesizing the new ferrous complex according to the present invention from 5-di(thiophen-2-yl)-1H-pyrrol-1-yl)-1,10-phenanthroline according to Example 1.

According to another aspect of the present invention, a method of preparing a ferrous complex represented by Chemical Formula 1 described above is provided, in which, as represented by the following Chemical Formula 2, thiophene is used as a starting material to synthesize 4-di(2-thienyl)-1,4-butanedione (FIG. 1), and then the 4-(di(2-thienyl)-1,4-butanedione thus synthesized is reacted with 1,10-phenanthrolin-5-amine to synthesize 5-di(thiophen-2-yl)-1H-pyrrol-1-yl)-1,10-phenanthroline (FIG. 2). The 5-di(thiophen-2-yl)-1H-pyrrol-1-yl)-1,10-phenanthroline and ethanol are used as a solvent to synthesize FeCl₃, and then 5-(2,5-di(thiophen-2-yl)-1H-pyrrol-1-yl)-1,10-phenanthroline Iron (III) Chloride represented by Chemical Formula 1 described above may be synthesized as a final product (FIG. 3).

According to another aspect of the present invention, a method of preparing a ferrous complex disclosed in claim 1 is provided, in which the method includes a) dissolving 4-di(2-thienyl)-1,4-butanedione, 1,10-phenanthrolin-5-amine, and p-toluene sulfonic acid in toluene, and then refluxing under nitrogen current; and b) dissolving the product obtained from the above step a) in ethanol, adding FeCl₃ dissolved in ethanol, and then reacting while stirring.

The 4-di(2-thienyl)-1,4-butanedione used in the above step a) may be commercially purchased. In addition, it may be prepared by dissolving thiophene and succinyl chloride in a reaction solvent, adding AgCl₃, and then reacting.

In addition, according to another aspect of the present invention, a biosensor including a ferrous complex represented by Chemical Formula 1 described above is provided. More specifically, a biosensor is provided including a substrate, an electrode including a working electrode and a reference electrode arranged on the substrate, an enzyme, and an electron transfer mediator, in which the electron transfer mediator is the ferrous complex represented by Chemical Formula 1 described above. The biosensor may be a glucose sensor.

The substrate may be a substrate that includes an electric insulation polymer resin.

The electrode detects an electrical signal generated by a reaction between an object to be measured and an enzyme, and may use a material such as carbon, gold, platinum, silver, copper, palladium, and the like. However, the present invention is not limited thereto. The electrode may include a working electrode and a reference electrode, and may further include an auxiliary electrode. The electrode may be formed by a method such as, a screen printing, an etching, a sputtering, and the like.

The enzyme and ferrous complex as an electron transfer mediator may be used as a biosensor, and for example, may be used as an enzyme reaction layer by applying the enzyme and ferrous complex on the top of the working electrode. In addition, the enzyme and ferrous complex may be used as special sequential layers by applying them on the top of the working electrode, and a combination layer of the enzyme and ferrous complex may be used.

The enzyme may be changed according to an object to be measured by a biosensor. For example, in a case in which cholesterol, alcohol, or glucose in blood is measured as an object, a cholesterol degrading enzyme, an alcohol degrading enzyme, or a glucose degrading enzyme may be used, respectively. Accordingly, in a glucose sensor according to an embodiment of the present invention, an enzyme for oxidizing glucose is used, such as, for example, an enzyme selected from the group consisting of glucose oxidase, glucose dehydrogenase, glucose hexokinase, glutamic oxaloacetic transaminase, and glutamic pyruvic transaminase. However, the present invention is not limited thereto.

BRIEF DESCRIPTION OF THE DRAWINGS

The above and other aspects, features and advantages of the present invention will be more clearly understood from the following detailed description taken in conjunction with the accompanying drawings, in which.

DETAILED DESCRIPTION OF EMBODIMENTS OF THE PRESENT INVENTION

Embodiments of the present invention are described in detail with reference to the accompanying drawings. The same reference numbers are used throughout the drawings and description to refer to the same or like parts. Detailed descriptions of well-known functions and structures incorporated herein may be omitted to avoid obscuring the subject matter of the present invention.

Advantages and features of the present invention and methods of accomplishing the same may be understood more readily by reference to the following detailed description of embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims.

Figure 4:
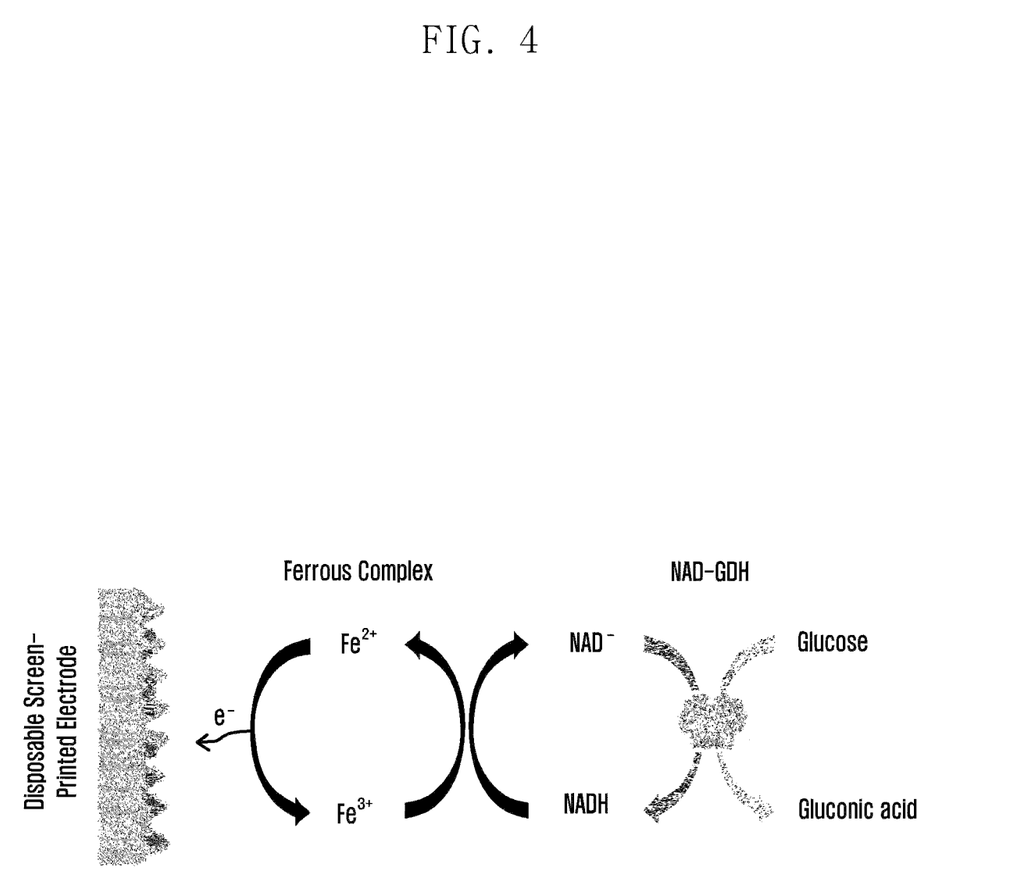
FIG. 4 is a diagram illustrating an example of a producing process and reaction route of a glucose sensor using the new ferrous complex according to the present invention as an electron transfer mediator.

FIG. 4 illustrates an example of a mechanism of the new ferrous complex according to the present invention, which functions as an electron transfer mediator for an enzyme-based glucose sensor. By electrons generated by oxidizing glucose with a glucose dehydrogenase (GDH), $NAD^+$ bonded to GDH is reduced to be NADH, and then the reduced NADH is oxidized into $NAD^+$ through an oxidation-reduction reaction with the ferrous complex according to the present invention, thereby simultaneously reducing the ferrous complex. At this time, the concentration of glucose is measured by measuring current generated by supplying the oxidation potential of the ferrous complex, which is an electron transfer mediator in a reduction state, on the surface of electrode.

Example 1

Preparation of New Ferrous Complex

Used Materials:
Thiophene, succinyl chloride, 1,10-phenanthrolin-5-amine, and p-toluene sulfonic acid (PTSA) were purchased from Sigma (USA). $AlCl_3$ was purchased from Junsei (Japan). Dichloromethane, toluene, and ethanol were purchased from Dae-Jung (Korea). NAD-GDH was purchased from Toyobo (Japan), and NAD and Nafion (5%) were purchased from Sigma (USA).

Step 1: Synthesis of 4-di(2-thienyl)-1,4-butanedione 120 mM thiophene and 50 mM succinyl chloride were dissolved in 100 ml of 99.8% dichloromethane as a reaction solvent, and then reacted for 10 minutes. Then, 16 g of $AgCl_3$ was added and reacted at 18° C. to 20° C. for 12 hours. The resulting product was washed with sodium bicarbonate and water, and treated with 5 g of $MgSO_4$ for removing the solvent to obtain a dark green product. Such a dark green product was washed with ethanol to obtain 4-di(2-thienyl)-1,4-butanedione that was a pale blue solid. The structure of the pale blue solid was confirmed by using 1H NMR. The spectroscopic data of the pale blue solid is as follows:

1H NMR: (400 MHz; $CDCl_3$) 3.40 (s, 4H), 7.15 (t, 2H), 7.68 (d, 2H), 7.82 (d, 2H)

Step 2: Synthesis of 5-di(thiophen-2-yl)-1H-pyrrol-1-yl)-1,10-phenanthroline 3.05 mM of the 4-di(2-thienyl)-1,4-butanedione obtained from Step 1 described above, 3.03 mM of 1,10-phenanthroline-5-amine, and 5.4 mM of p-toluene sulfonic acid were dissolved in toluene, and then refluxed under a nitrogen current for 4 days. The refluxed mixture was cooled to room temperature, and then toluene was removed from the mixture. The remaining material was dissolved in 5 ml of 99.8% dichloromethane solution, and eluted by using a silica column to obtain 5-di(thiophen-2-yl)-1H-pyrrol-1-yl)-1,10-phenanthroline. The yield was 85%, and the structure was confirmed by using 1H NMR. The spectroscopic data thereof is as follows:

1H NMR: (400 MHz; $CDCl_3$) δ 9.29-9.27 (dd, 1H), 9.17-9.15 (dd, 1H), 8.29-8.25 (dd, 1H), 7.99 (s, 1H), 7.73-7.66 (m, 2H), 7.54-7.50 (dd, 1H), 6.89-6.87 (m, 2H), 6.65-6.62 (m, 2H), 6.51-6.50 (dd, 1H)

Step 3: Synthesis of 5-(2,5-di(thiophen-2-yl)-1H-pyrrol-1-yl)-1,10-phenanthroline Iron (III) Chloride 2.4 mM of the 5-di(thiophen-2-yl)-1H-pyrrol-1-yl)-1,10-phenanthroline obtained from Step 2 described above was dissolved in 20 ml of 99.5% ethanol, added to 20 ml of ethanol dissolved with 2.5 mM of $FeCl_3$, and then reacted at a room temperature for 1 hour while stirring. The floating material was filtered, the remaining solid was washed with ethanol, and then vacuum-dried to obtain 5-(2,5-di(thiophen-2-yl)-1H-pyrrol-1-yl)-1,10-phenanthroline Iron (III) Chloride that was a new ferrous complex as a final product. The structure of the final product was confirmed by using a mass spectrometer. The spectroscopic data thereof is as follows:

MS (EI) mz-1: 321 (5%), 285 (10%), 229 (30%), 196 (60%), 195 (100%), 168 (58%), 167 (32%), 140 (25%)

Example 2

Manufacture of Glucose Sensor using Ferrous Complex According to the Present Invention 1.0 μl of a solution that was prepared by dissolving 1.0 mM of the ferrous complex prepared according to Example 1 as described above in 99.5% ethanol was dropped on the top of a working electrode formed of a screen-printed carbon electrode (SPCE), and then dried at a room temperature for 30 seconds. 1.0 µl of 4.0 mg/ml solution that was prepared by dissolving NAD-glucose dehydrogenase (NAD-GDH) in distilled water was dropped on the dried electrode, and then dried at room temperature for 30 seconds. 1.0 µl of 1.0% Nafion solution was dropped thereon to form a protective layer of the ferrous complex and NAD-GDH. As a result, a glucose sensor was manufactured. As electrode of the glucose sensor, screen-printed carbon electrode including the working electrode, an auxiliary electrode, and a reference electrode was used, in which the working electrode and auxiliary electrode were manufactured by using a carbon ink, and the reference electrode was manufactured by using a silver ink.

Comparative Example 1

Manufacture of Glucose Sensor Using Ferricyanide

A glucose sensor was manufactured by using ferricyanide through the same method as Example 1 as described above, except that 1.0 µl of 1.0 mM ferricyanide (Sigma, Potassium ferricyanide (III)) was used instead of the ferrous complex used in Example 1.

Experimental Example 1

Experiment for Measuring Oxidation-Reduction Current of Ferrous Complex According to Scanning Speed In order to confirm a change in the relationship of oxidation-reduction current according to a change of potential scanning speed of the new ferrous complex according to the present invention, the following experiment was performed. 1.0 mM ferrous complex prepared according to Example 1 was dissolved in a solution of dimethyl sulfoxide (DMSO)/0.1M tetrabutyl ammonium perchlorate (TBAP), and a change of oxidation-reduction current was measured by changing the scanning speed from 10 mV/s to 250 mV/s at a potential range of 0.0 V to 0.8 V by cyclic voltammetry using a glassycarbon electrode. The results are shown in FIG. 5.

Figure 5:
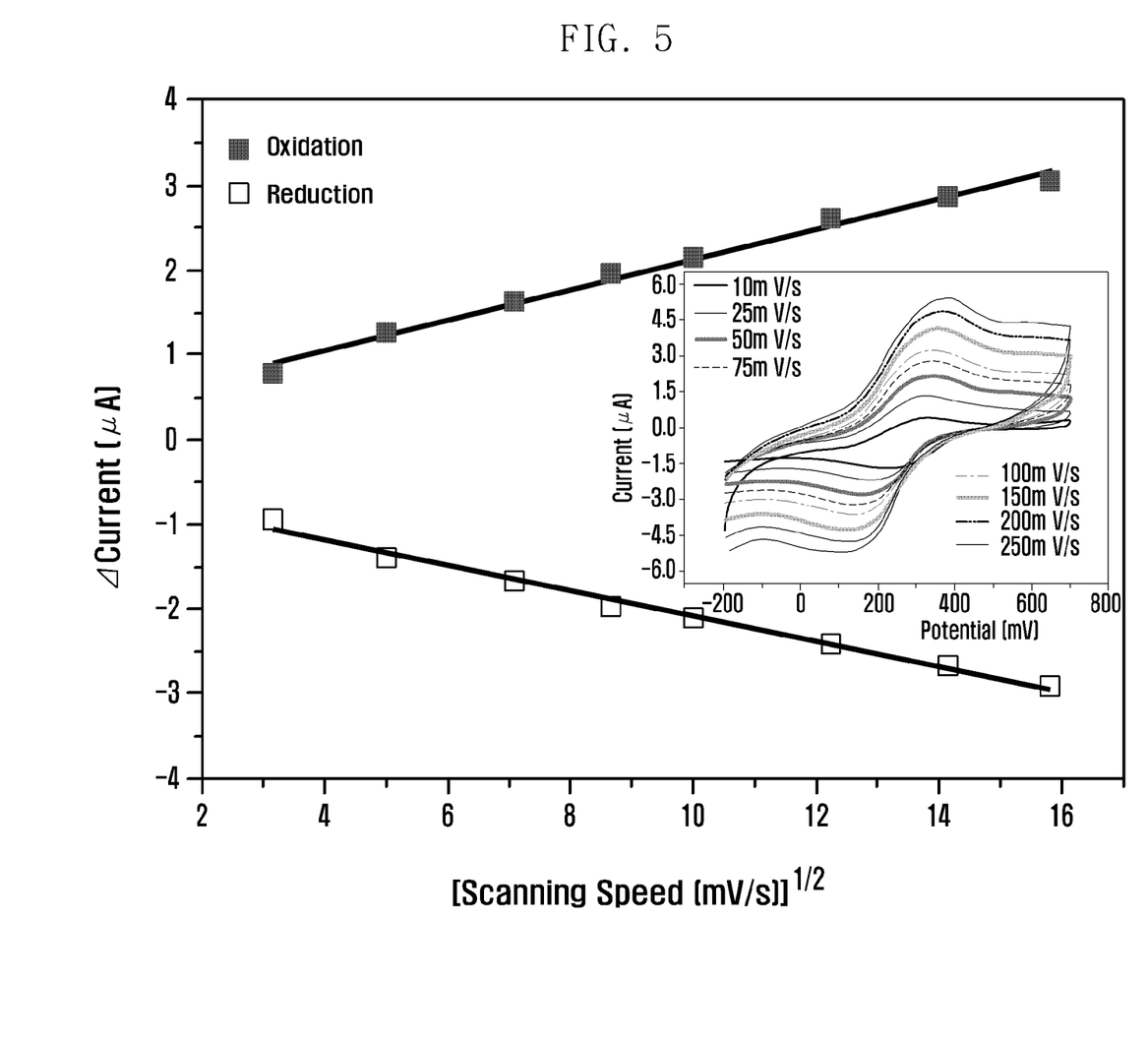
FIG. 5 is a graph illustrating an increase of oxidation-reduction current of the ferrous complex according to the present invention according to an increase of scanning speed.

From the result in FIG. 5, it can be confirmed that the oxidation-reduction current value of the ferrous complex according to the present invention is proportional to the square root of the scanning speed.

In addition, from the above results, the electron transfer rate of the ferrous complex according to the present invention is calculated based on the following Equation (1).

$$\psi = \Lambda \pi^{-1/2} = \frac{(D_O/D_R)^{\alpha/2} k^0}{(\pi D_O f v)^{1/2}} \quad (1)$$

where, $\psi$ represents an equilibrium parameter constant, $D_o$ ($1.52 \times 10^{-7}$) and $D_R$ ($1.58 \times 10^{-7}$) represent diffusion coefficients, v represents a scanning speed, f=F/RT, F represents a parameter constant, R represents a gas constant, and T represents an absolute temperature.

$\alpha$ (0.5) represents a coefficient of transmission. When the value of $\alpha$ is between 0.3 and 0.7, $\Delta Ep$ is irrelevant to $\alpha$, but depends on only $\psi$. When the scanning speed is 50 mV/s, $\Delta Ep$ is 98.2 mV/s. When $\Delta Ep$ is 98.2 mV/s, $\psi$ corresponds to 0.75. The electron transfer rate, $k^0$ of the ferrous complex according to the present invention, which is calculated by using Equation (1) as described above, is 0.023 cm/s.

Experimental Example 2

Comparison of Oxidation Current of Glucose Sensor Using Ferrous Complex According to the Present Invention or Ferricyanide as Electron Transfer Mediator A solution prepared by dissolving 5 mM glucose in 0.1 M phosphate buffer solution (pH 7.4) was applied to the glucose sensors manufactured according to Example 2 and Comparative Example 1 as described above. The glucose oxidation current was measured at a potential range of 0.0 V to 0.8 V and a scanning speed of 100 mV/s by cyclic voltammetry. The results are shown in FIG. 6.

Figure 6:
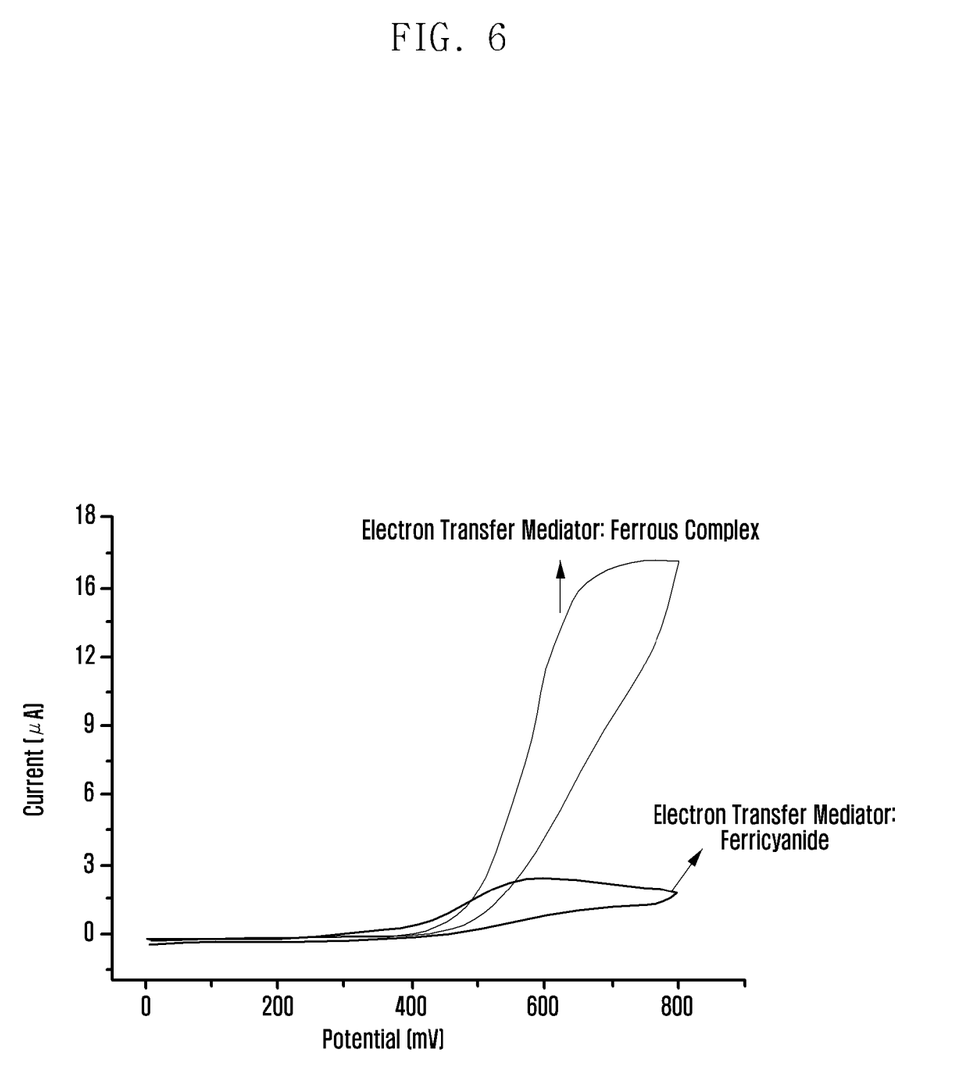
FIG. 6 is a graph illustrating cyclic voltammograms of a glucose sensor using the ferrous complex according to the present invention (Example 2) and a glucose sensor using ferricyanide (Comparative Example 1) in the concentration of 5 mM glucose.

From the results in FIG. 6, it can be confirmed that in the case of Example 2, which is a glucose sensor using the ferrous complex according to the present invention as an electron transfer mediator, the oxidation current is about five times higher than in the case of Comparative Example 1, which is a glucose sensor using ferricyanide, which is a conventional electron transfer mediator.

Experimental Example 3

Evaluation of Glucose Oxidation Current in Glucose Sensor According to Glucose Concentration Glucose solutions with concentrations of 1 mM, 5 mM, 10 mM, 20 mM and 30 mM, which were prepared by dissolving the glucose in 0.1 M phosphate buffer solution (pH 7.4), were applied to the glucose sensors manufactured according to Example 2 and Comparative Example 1 as described above. The glucose oxidation current was measured at a potential range of 0.0 V to 0.8 V and a scanning speed of 100 mV/s by cyclic voltammetry. The results are shown in FIGS. 7A to 7C.

Figure 7A:
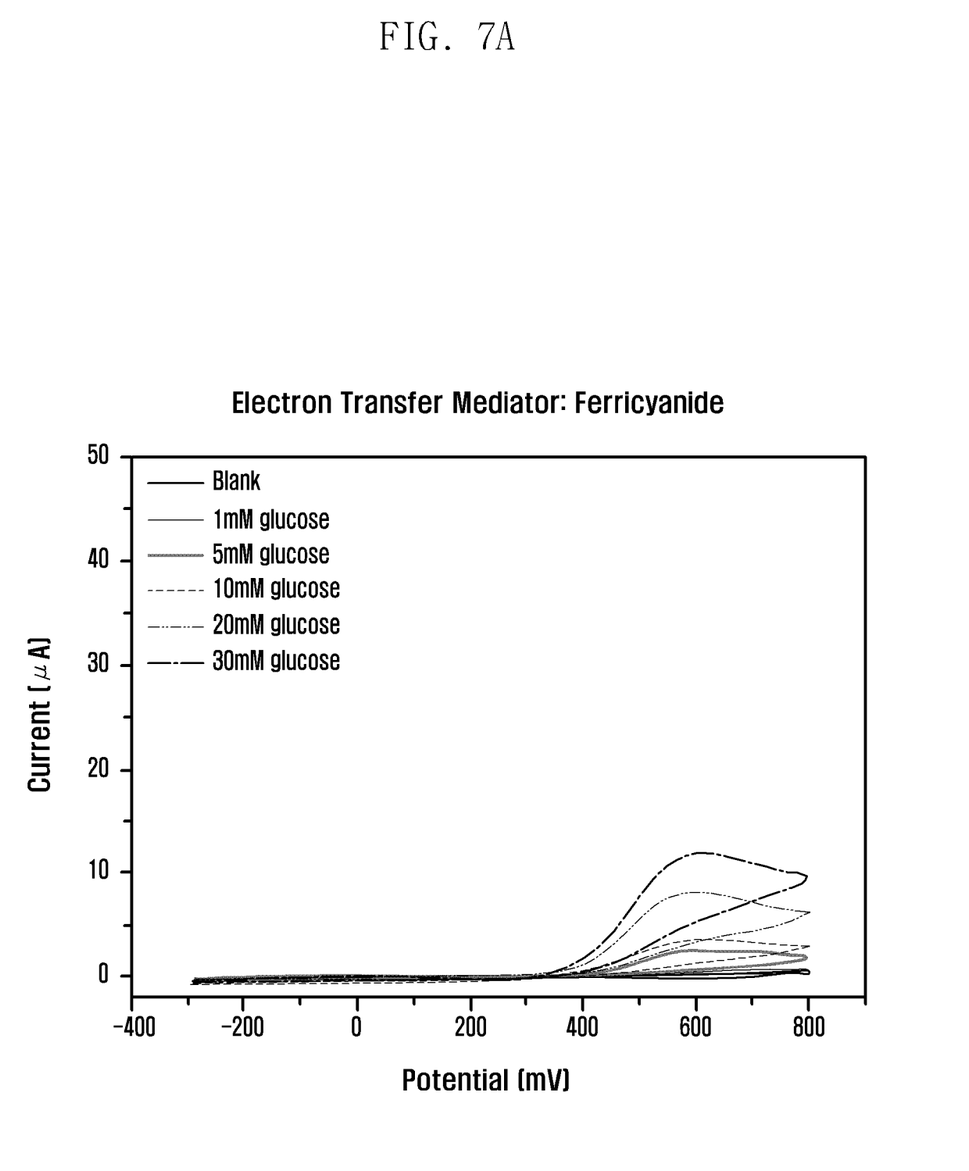
FIGS. 7A to 7C are graphs illustrating standard calibration curves of a glucose sensor using the ferrous complex according to the present invention (Example 2) and a glucose sensor using ferricyanide (Comparative Example 1) at various glucose concentrations.
Figure 7B:
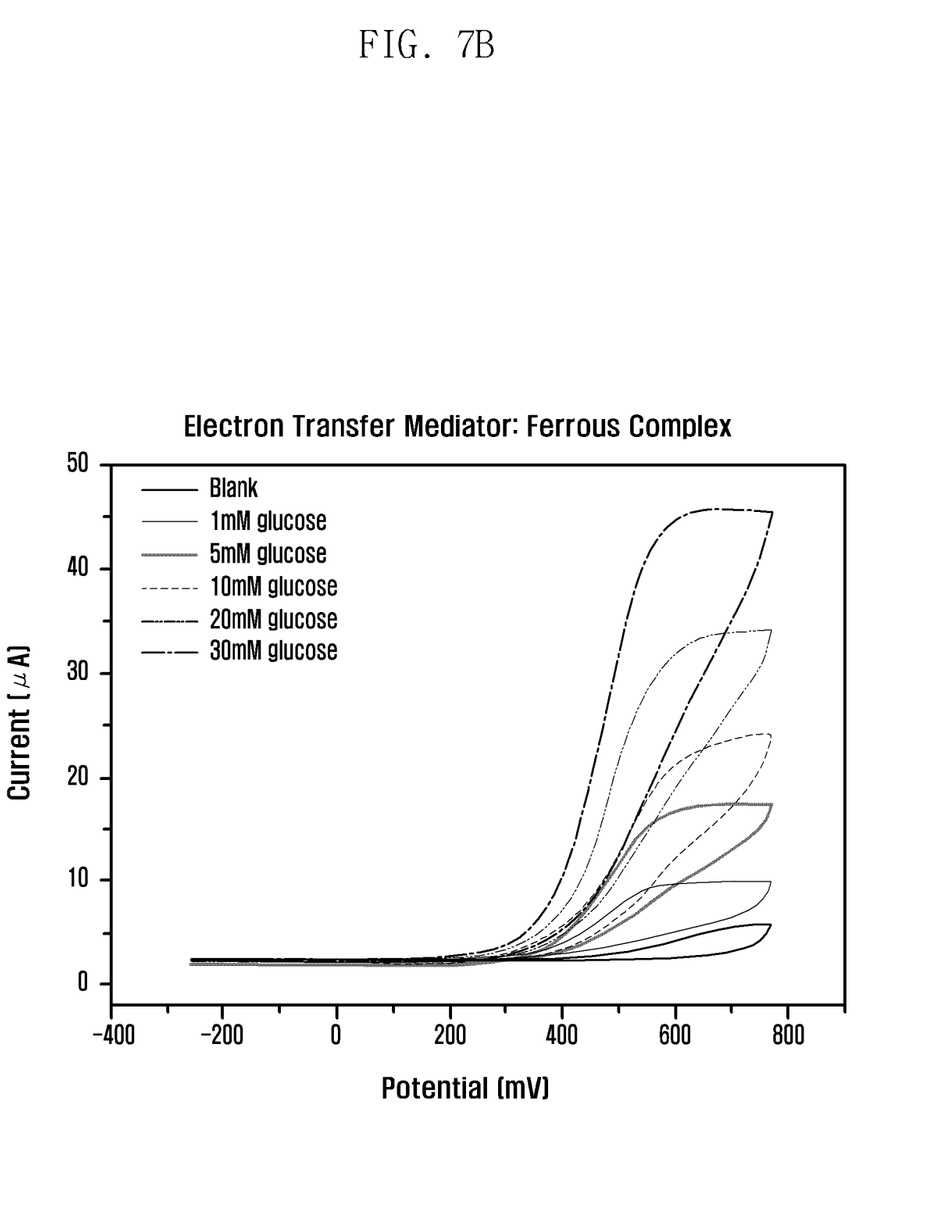

From the results in FIG. 7B, it can be confirmed that in the case of Example 2, which is a glucose sensor using the ferrous complex as an electron transfer mediator, the oxidation current was significantly higher compared with that obtained with Comparative Example 1, as shown in FIG. 7A, which is a glucose sensor using ferricyanide, which is a conventional electron transfer mediator.

Figure 7C:
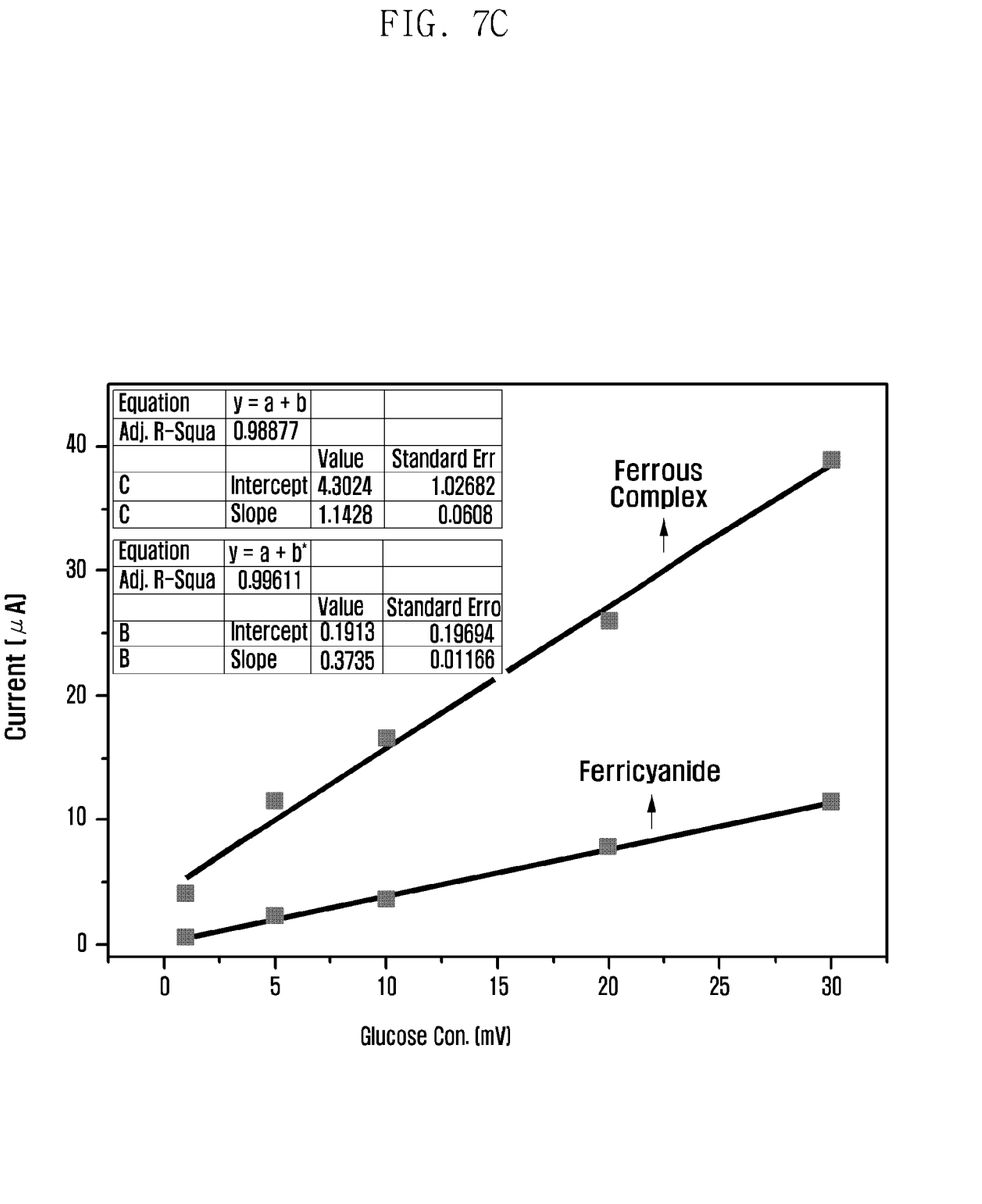

In addition, from the gradient in FIG. 7C, it can be confirmed that in the case of the new electron transfer material synthesized from the present invention, the detection sensitivity of glucose is improved by about three times as compared with the method using ferricyanide, which is a conventional electron transfer mediator.

Figure 8:
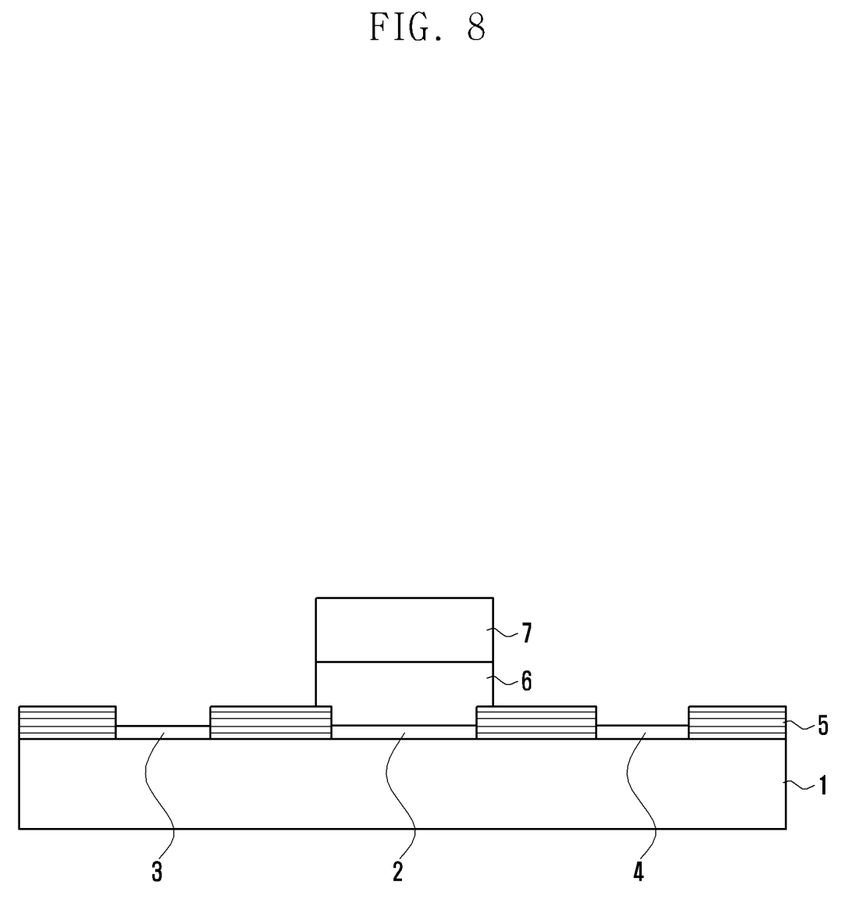
FIG. 8 is a schematic diagram illustrating a cross-section of the biosensor according to an embodiment of the present invention.

FIG. 8 is a schematic diagram illustrating a cross section of the biosensor according to an embodiment of the present invention. As described above, the biosensor includes an insulating substrate 1 including electrodes thereon, working electrode 2, reference electrode 3, and auxiliary electrode 4 for detecting an electrical signal generated by the reaction between an object to be measured and an enzyme, and an enzyme reaction layer 6 including a ferrous complex and an enzyme arranged on the top of the working electrode and reference electrode. Further, the biosensor may include an insulating film 5 to coat the part of the biosensor other than the top of the electrodes in order to create an insulation between each electrode, and also may further include a protective layer 7 for protecting the enzyme reaction layer 6 formed on the top of the enzyme and ferrous complex. However, the configuration of the biosensor is not limited to the structure as illustrated in FIG. 8.

As set forth above, according to embodiments of the present invention, the new ferrous complex is strongly absorbed into the electrodes of a biosensor, and thereby can function as a stable electron transfer mediator, so that in a case in which the new ferrous complex is applied to a biosensor as an electron transfer mediator, the biosensor can exhibit improved sensitivity and excellent performance as compared with the case of using the conventional electron transfer mediator, and thus can provide more accurate and precise measurements.

While the present invention has been shown and described in connection with the certain embodiments, it will be apparent to those skilled in the art that modifications and variations can be made without departing from the spirit and scope of the invention as defined by the appended claims.

What is claimed is:

1. A biosensor comprising a substrate, a working electrode and a reference electrode arranged on the substrate, an enzyme, and an electron transfer mediator, the electron transfer mediator being a ferrous complex represented by the following Chemical Formula 1:

[Chemical Formula 1]

2. The biosensor according to claim 1, wherein the working electrode and the reference electrode are selected from the group consisting of carbon, gold, platinum, silver, copper, and palladium.

3. The biosensor according to claim 1, wherein the biosensor is a glucose sensor.

4. The biosensor according to claim 2, wherein the biosensor is a glucose sensor.

5. The biosensor according to claim 3, wherein the enzyme is selected from the group consisting of glucose oxidase, glucose dehydrogenase, glucose hexokinase, glutamic oxaloacetic transaminase, and glutamic pyruvic transaminase.

6. The biosensor according to claim 4, wherein the enzyme is selected from the group consisting of glucose oxidase, glucose dehydrogenase, glucose hexokinase, glutamic oxaloacetic transaminase, and glutamic pyruvic transaminase.

7. A ferrous complex represented by the following Chemical Formula 1:

[Chemical Formula 1]

8. The ferrous complex according to claim 7, wherein the ferrous complex is an electron transfer mediator of an enzyme-based biosensor.

9. The ferrous complex according to claim 8, wherein the biosensor is a glucose sensor.

10. The ferrous complex according to claim 9, wherein the enzyme is selected from the group consisting of glucose oxidase, glucose dehydrogenase, glucose hexokinase, glutamic oxaloacetic transaminase, and glutamic pyruvic transaminase.

11. A method for preparing a ferrous complex as disclosed in claim 7, the method comprising:
   a) dissolving 4-di(2-thienyl)-1,4-butanedione, 1,10-phenanthrolin-5-amine, and p-toluene sulfonic acid in toluene, and then refluxing under a nitrogen current; and
   b) dissolving the product obtained from the above step a) in ethanol, adding $FeCl_3$ dissolved in ethanol, and then reacting while stirring.

12. The method for preparing the ferrous complex according to claim 11, wherein the 4-di(2-thienyl)-1,4-butanedione in step a) is prepared by dissolving thiophene and succinyl chloride in a reaction solvent, adding $AgCl_3$, and then reacting.

* * * * *